United States Patent [19]

Mitchell et al.

[11] 4,441,514

[45] Apr. 10, 1984

[54] SMOKE FLAVOR ENHANCING AGENTS

[75] Inventors: Terence G. Mitchell, Romsey; Adrian G. Barnes, Fareham; Julia S. Jackson; Peter C. Bevan, both of Southampton, all of England

[73] Assignee: British-American Tobacco Co., Ltd., London, England

[21] Appl. No.: 338,897

[22] Filed: Jan. 12, 1982

[30] Foreign Application Priority Data

Jan. 19, 1981 [GB] United Kingdom ............... 8101536

[51] Int. Cl.$^3$ .......................... A24B 3/12; A24B 15/30
[52] U.S. Cl. .................................................. 131/276
[58] Field of Search ................................. 131/274–279

*Primary Examiner*—V. Millin
*Attorney, Agent, or Firm*—Kane, Dalsimer, Kane, Sullivan and Kurucz

[57] ABSTRACT

This invention relates to a method for enhancing the smoke flavor of a smoking material by treating the said material with an agent comprising 3-hydroxsclareol, particularly with the compound 3β-hydroxysclareol. The invention further relates to the smoke-enhancing agent and a method by which it can be obtained by subjecting sclareol to a microbial transformation process. Finally it extends to smoking material incorporating the said agent.

10 Claims, No Drawings

SMOKE FLAVOR ENHANCING AGENTS

BACKGROUND OF THE INVENTION

1. Field of the Invention

This invention relates to smoke-flavour enhancing agents, a method of manufacture thereof and a method of enhancing the smoke flavour of a smoking material.

2. Brief Description of the Prior Art

Flavour-enhancing agents may themselves contribute to the smoke flavour of a smoking material, but the present invention is more especially concerned with the provision of agents whose effect is to enhance the characteristic flavour of the smoking material itself, particularly a tobacco-characteristic flavour, without introducing undesirable flavour attributes. Apart from the evident possibility of obtaining new flavours or flavour tones, such agents provide an additional tool for the assistance of the tobacco blender whereby control for the attainment of a desired smoke-flavour can be exercised more reliably and/or with greater economy.

Compounds chemically related to sclareol and said to be useful as additives to tobacco are disclosed in United Kingdom Patent Specification No. 847,201 and U.S. Pat. No. 3,050,532. These compounds are disclosed as obtained by subjecting sclareol to chemical conversion processes.

Sclareol is a diterpene compound which is obtainable from the flowers of the Clary sage (*Salvia sclarea*) and from the flowers and leaves of *Nicotiana glutinosa*. A process for recovering sclareol from Clary sage is disclosed in U.K. Specification No. 879,958.

SUMMARY OF THE INVENTION

According to the present invention, a group of compounds valuable for enhancing the smoke flavour of smoking material are obtained by subjecting sclareol to a microbial transformation process.

Also according to the invention, a smoke-flavour enhancing agent for incorporation with a smoking material comprises one or more compounds from the group consisting of 3α-hydroxysclareol, 3β-hydroxysclareol and 3-oxosclareol.

The invention also provides a method of manufacture of a smoke flavouring agent for incorporation with a smoking material, wherein sclareol is contacted with a microbial culture to effect a transformation of at least a proportion of the sclareol to a product comprising 3-hydroxysclareol. The hydroxysclareol may be 3α-hydroxysclareol or 3β-hydroxysclareol, and the product may be further comprise 3-oxosclareol.

A product comprising these three compounds may be used as a tobacco-smoke flavour-enhancing agent. Alternatively, one or more of the compounds, advantageously being or including the more potent and higher-yielding 3β-hydroxysclareol, may be first extracted and the extracted compound or compounds used as tobacco-smoke flavour enhancing agent or agents.

DETAILED DESCRIPTION OF THE INVENTION

The invention further provides a method of enhancing the smoke flavour of a smoking material, wherein there is incorporated with the smoking material an agent comprising one or more compounds selected from the group consisting of 3α-hydroxysclareol, 3β-hydroxysclareol and 3-oxosclareol. The smoking material may be tobacco, a reconstituted tobacco material or a tobacco substitute material. Advantageously, the agent is or comprises 3β-hydroxyclareol. The agent may be incorporated with a smoking material by being sprayed thereon in volatile solvent or by being sprinkled thereon in fine crystalline granular form. In the latter case a binder may be employed to bind the crystals to the smoking material. The agent is suitably added to the smoking material at a loading level within a range of 50 to 2,000 parts per million of tobacco.

The chemical structure of 3α-hydroxysclareol may be represented as:

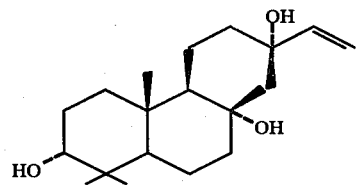

The chemical structure of 3β-hydroxysclareol may be represented as:

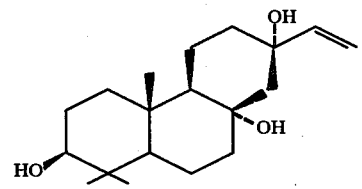

The chemical structure of 3-oxosclareol may be represented as:

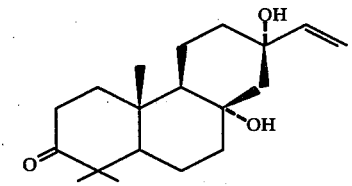

We have discovered that a wide range of micro-organisms, including fungi and bacteria, may be used in the transformation of sclareol to a product comprising 3α-hydroxysclareol and 3β-hydroxysclareol. In some cases 3-oxosclareol also is produced. Of fifty fungal shake-flask cultures derived from a sample of air-cured leaf tobacco it was found that twenty-eight were effective in transforming sclareol to give 3-hydroxysclareol, although considerable variations in extent of conversion were found. With each of the twenty-eight fungi 3β-hydroxysclareol was produced and with eighteen of these twenty-eight fungi 3β-hydroxysclareol was also found to be present. With thirteen of these twenty-eight fungi 3-oxosclareol was found to be present. Seventeen of these fungi were identified as species of Aspergillus (8 strains), Penicillium (3 strains), Cladosporium (1 strain), Alternaria (1 strain), Nodulisporium (1 strain), Ulocladium (1 strain), Fusarium (1 strain) and Phoma (1 strain). Eleven fungi could not be identified due to lack of sporulation. Examples of suitable micro-organisms are:

*Ophiobolus herpotrichus* (CBS 240.31)
*Alternaria alternata* F316 (CBS 547.80)
*Cladosporium oxysporum* F312 (CBS 548.80)

*Penicillium thomii* F309 (CBS 549.80)
*Bacillus pumilus* (NCIB 11617)

The *Ophiobolus herpotrichus* is obtainable from the Centraalbureau Voor Schimmelcultures, Oosterstraat 1, Baarn, Holland. The culture deposits having the accession numbers CBS 547.80, CBS 548.80 and CBS 549.80 were each made with the Centraalbureau Voor Schimmelcultures on May 25, 1980. The respective characteristics of the fungi the subjects of these three deposits are given in Table 1 below.

Culture deposit NCIB 11617 was made on Nov. 14, 1980 at the National Collection of Industrial Bacteria, Torry Research Station, 135 Abbey Road, Aberdeen, Scotland. The characteristics of the *Bacillus pumilus* NCIB 11617 are:

Morphology: Slender gram variable rods with elliptical central endospores not swelling the sporangium.

Temperatures for growth: Good growth at 30°, 37°, 50°, no growth at 55° C.

Growth characteristics (nutrient agar 30° C.): Colonies 1.5 mm flat, smooth, off-white, opaque, irregular and slightly erose.

| Biochemical characteristics: | |
|---|---|
| Catalase | + |
| Oxidase (Kovacs) | + |
| Anaerobic growth | − |
| Growth in 5% NaCl | + |
| Growth in 7% NaCl | + |
| Gas from glucose | − |
| Acetoin production | + |
| Casein decomposition | + |
| Gelatine decomposition | + |
| Starch hydrolysis | − |
| Nitrate reduction | − |
| Indole | − |
| Citrate | − |
| Arginine dehydrolase | − |
| pH in VP broth | 5.2 |

On the basis of these characteristics the isolate was considered to conform to the description of *Bacillus pumilus* given by Bergey's Manual of Determinative Bacteriology, 8th Edition (1974).

The selection of micro-organisms which possess the property of transforming sclareol to yield 3α-hydroxysclareol and 3β-hydroxysclareol was made by incubating sclareol with a range of micro-organisms obtained from culture collections and by direct isolation from natural substances such as soil and tobacco leaves. The novel products were identified by comparing extracts from the culture media with controls comprising culture media having no sclareol. The products were then isolated and purified and predetermined proportions thereof were incorporated with cigarette tobacco.

Cigarettes filled with this tobacco were smoked by an expert panel of smokers to assess the effect of the respective products on the tobacco smoke. In all cases, smokers noted an appreciable effect upon the flavour of the smoke, but without the intrusion of any undesirable smoke attribute. In general the effect observed was an enhancement of the smoke flavour characteristically associated with the particular tobacco.

The sclareol used in each of the following examples was obtained from commercial grade Clary sage absolute supplied by Payan & Bertrand of Grasse, France. The absolute was first filtered under negative pressure to remove liquid and the solid was then washed with a stream of ice-cold n-hexane at room temperature until the original green colour was totally removed. The remaining white solid was determined to be sclareol. Additional amounts of sclareol were recovered from the hexane washings by crystallation. The yield of sclareol averaged about 20% by weight of the original absolute. As will be appreciated, sclareol derived from *Nicotiana glutinosa* could equally well be used for the purpose of the present invention.

The following examples illustrate procedures for obtaining the sclareol compounds and the nature of the products obtained:

EXAMPLE 1

A pure culture of *Ophiobolus herpotrichus* CBS 240.31 was inoculated into two 250 ml Erlenmeyer flasks each containing 100 ml sterile malt extract broth of formula:
Malt extrct: 17 g
Mycological peptone: 3 g
Distilled water: 1000 ml
pH: 5.4

The flasks were incubated on an orbital shaker at room temperature, with a shaker speed of 150 rpm, for seven days in order to obtain a growth of *O. herpotrichus*. 200 mg of sclareol dissolved in ethanol was then added to one of the two flasks and in equal quantity to a third flask containing 100 ml of the sterile malt extract but no fungus. Incubation of all three flasks was continued for a further seven days after which the content of each flask was extracted with chloroform. After concentration, the extracts from the three flasks were compared with each other by means of thin layer chromatography (TLC), using silica gel plates and a 9:1 chloroform/methanol solvent. For visualisation purposes, the plates were sprayed with a mixture of anisaldehyde and sulphuric acid and then heated. In the case of the extract from the flask in which sclareol was added to the fungus culture, the TLC procedure indicated the presence of three diterpene compounds additional to sclareol. These compounds were not present in the extracts from the other two flasks. It was thus concluded that the three additional diterpene compounds had resulted from a transformation of the sclareol brought about by the *O. herpotrichus* fungus. The three additional diterpene compounds visualised were all more polar than sclareol by Rf value in the TLC system:
Compound I: Rf 0.10
Compound II: Rf 0.17
Compound III: Rf 0.26
Sclareol: Rf 0.33

Compounds I, II and III were separated by a combination of column, high pressure liquid and thin layer chromatography and each was then identified using gas chromatography-mass spectrometry, nuclear magnetic resonance and infra-red analysis. The following identities were established:
Compound I: 3α-hydroxysclareol
Compound II: 3β-hydroxysclareol
Compound III: 3-oxosclareol

EXAMPLE 2

*O. herpotrichus* was grown in 100 ml sterile malt extract according to the procedure of Example 1. To the culture there was then added 100 mg of sclareol dissolved in ethanol. At the conclusion of a further three days incubation period, the presence of Compounds I, II and III and residual sclareol was demonstrated.

EXAMPLE 3

The procedure of Example 2 was followed except that incubation after the addition of sclareol proceeded for periods of seven and eleven days. At the conclusion of each of these incubation periods the presence of Compounds I, II and III and residual sclareol was demonstrated.

EXAMPLE 4

The procedure of Example 2 was repeated excepting in that 400 mg of sclareol was employed and incubation was extended to ascertain that incubation period resulting in the optimum yield rate of Compounds I, II and III. It was observed that the development of the Compounds I, II and III and that of the fungus peaked at about ten to twelve days of incubation.

EXAMPLE 5

The procedure of this example was as per Example 2 but to the fungus culture was added 400 mg sclareol dissolved in polyoxyethylene (20) sorbiton monooleate, supplied by Sigma Chemicals, Poole, England under the trade name "Tween 80". At the conclusion of a three day incubation period from the addition of sclareol, Compounds I, II and III were identified as present, the yield of Compounds I and II amounting together to 12% by weight of the original sclareol.

EXAMPLE 6

The Example 5 procedure was repeated but with an incubation period extended to seven days. The yield of Compounds I and II was found to be 36% of the original sclareol.

EXAMPLE 7

The Example 5 procedure was repeated but with a ten day incubation period, at the conclusion of which Compounds I and II were recovered at 23% of the original sclareol.

EXAMPLE 8

*O. herpotrichus* was grown in a number of flasks, each containing 100 ml sterile malt extract broth of the formula given for Example 1, for four days on an orbital shaker. To each flask there was then added 200 mg sclareol dissolved in "Tween 80". After an incubation period of three days Compounds I and II were found to be present at a total weight of 110 mg, i.e. 55% that of the added sclareol.

EXAMPLE 9

The procedure was as per Example 8 but with an incubation period of seven days. Compounds I and II were then found to be present at a total weight of 134 mg, i.e. 67% that of the added sclareol.

EXAMPLE 10

The procedure of Example 8 was followed except that the incubation period was ten days, after which the total weight of the Compounds I and II was found to be 52 mg, i.e. 26% of the added sclareol.

EXAMPLE 11

2.5 l sterile malt extract broth in a 3 l fermenter vessel was innoculated with *O. herpotrichus* and incubated at 23° C. with continuous stirring at 300 rpm and aeration. After three days 6 g sclareol dissolved in "Tween 80" was added. The incubation was then continued for a further five days, at the end of which period Compounds I and II were found to be present in the broth and 2 g of Compound II were recovered from the broth.

EXAMPLE 12

The general procedure of Example 11 was followed but a 20 l vessel containing 15 l sterile malt extract broth was used. 45 g sclareol in "Tween 80" was added and the broth stirred at 400 rpm and aerated at 5.8 l/min. Compounds I, II and III were recovered by extraction of the liquid at the end of the experiment. The greater part of the unreacted sclareol was obtained in extraction of the fungal growth.

EXAMPLE 13

The procedure of Example 9 was repeated using a pure culture of *Alternaria alternata* CBS 547.80 in place of *O. herpotrichus*. At the conclusion of the seven day incubation period the Compounds I, II and III were found to be present and were separated from the culture medium.

EXAMPLE 14

The procedure followed was the same as that of Example 13 except that the micro-organism used was *Cladosporium oxysporum* CBS 548.80. Compounds I and II were found to be present at the end of the incubation period and were recovered from the culture medium.

EXAMPLE 15

The procedure of Example 13 was again repeated, the micro-organism this time used being *Penicillium thomii* CBS 549.80. Compounds I, II and III were found to be present and were separated from the culture medium.

EXAMPLE 16

A pure culture of *Bacillus pumilus* NCIB 11617 was grown in an Erlenmeyer flask containing 100 ml nutrient broth designated CMI and supplied by Oxoid Limited, Basingstoke, England. After a seven day growth period, on an orbital shaker at room temperature, 100 mg sclareol dissoled in 0.4 ml "Tween 80" was added. Incubation was then continued for a further seven days, after which the culture was extracted. It was shown that Compounds I, II and III had been formed.

It is a particular merit of the newly identified and produced compounds that they enhance the tobacco-like character of the smoke from cigarettes. This is in contrast to many well known substances with flavour properties, including other derivatives of sclareol, which impart distinctive flavour characters, described as floral or woody, to tobacco smoke, but without significantly increasing the tobacco character.

A discovery made with the new compounds is an ability to boost the natural tobacco smoke aroma when added to cigarette tobacco at levels between 50 and 2000 p.p.m. and particularly between 50 and 250 p.p.m. This discovery is of especial value when applied to cigarettes containing a preponderance of air-cured tobacco and to blended cigarettes, that is cigarettes containing mixtures of flue-cured, air-cured and oriental tobacco in varying proportions. In addition, it is useful in designs of cigarettes of lower tar delivery in which the natural level of tobacco flavour is perceived as low by the smoker.

TABLE 1

The characteristics of the culture deposits with the accession numbers CBS 549.80, CBS 548.80 and CBS 547.80 referred to above are tabulated below in respect of the following:
I. Temperature range for growth.
II. Growth on potato dextrose agar at 25° C.
III. Growth on malt extract agar at 25° C.
IV. Microscopic characteristics.

CBS 549.80 *Penicillium thomii*

I. Growth at 20° C. and 30° C. No growth at 37° C.
II. At 4 days, colony 26 mm diameter, flat granular to powdery white with smoke-grey areas and cream reverse. At 12 days, 65 mm diameter, some radial zonation, smoke-grey with white margin and buff reverse.
III. At 4 days, white, 20 mm diameter, flat powdery to granular with ochreous reverse. At 12 days, 65 mm diameter, smoke-grey, white margin, ochreous reverse.
IV. Abundant hard, gritty, sclerotia produced over entire surface. No ascomata. Conidial heads phialides, penicillate, monoverticillate. Condiophores smooth-walled 90–150µ long. Sterigmate bottle shaped 7–12µ, condia elliptic, smooth 1.2–2.9µ in long chains.

CBS 548.80 *Cladosporium oxysporum*

I. Growth at 20° C. and 30° C. No growth at 37° C.
II. At 4 days, 24 mm diameter, cottony to velvety growth, dark herbage green with dull green reverse. At 12 days, 70 mm diameter, velvety, grey olivaceous with paler margin and dull green reverse.
III. At 4 days, 21 mm diameter, raised cottony to velvety, furrowed, glaucous-grey with cream-white margin. Reverse fuscous black with cream margin. At 12 days, 52 mm diameter, radially furrowed, cottony/velvet glaucous-grey with pale margin and fuscous black reverse.
IV. Brown-pigmented smooth condiophores 65–95µ long, swollen at apex. Branching tree-like from apex into non-septate smooth blastospores 2.2–4.2µ in branching chains 'Scar' at points of detachment of blastospores.

CBS 547.80 *Alternaria alternata*

I. Growth at 20° C. and 30° C. No growth at 37° C.
II. At 14 days, 72 mm diameter, cottony growth, irregular margin, pale olivaceous grey with dull green reverse.
III. At 14 days, 73 mm diameter, cottony to floccose with finely indented margin. Smoke-grey with reverse centre sepia shading to amber at margin.
IV. Condia brown, muriform arising in chains from simple pigmented condiophores. Condia ovoid, tapering at end distal from condiphore origin, usually to terminal paler beak-like cell. condia 13µ×21µ.

What is claimed is:

1. A method for enhancing the smoke flavour of a smoking material which comprises incorporating with the material a product comprising 3-hydroxysclareol.

2. A method according to claim 1 wherein the 3-hydroxysclareol is 3-β-hydroxysclareol.

3. A method according to claim 1 wherein the product comprises at least one compound selected from the group consisting of 3α-hydroxyclareol, 3β-hydroxysclareol and 3-oxosclareol.

4. A method for enhancing the smoke flavour of a smoking material which comprises incorporating with the material, a product obtained by subjecting sclareol to a microbial transformation process whereby at least a portion of the sclareol is transformed to a compound selected from the group consisting of 3α-hydroxysclareol, 3β-hydroxysclareol and 3-oxosclareol.

5. A smoking material obtained by the method according to claim 1.

6. A smoking article comprising smoking material obtained by the method according to claim 1.

7. A method for the production of a smoke-flavour enhancing agent for incorporation with a smoking material, which comprises contacting sclareol with a microbial culture to effect a transformation of at least a proportion of the sclareol to a product comprising 3-hydroxysclareol.

8. A method according to claim 7, wherein said product comprises at least one compound of the group consisting of 3α-hydroxysclareol, 3β-hydroxysclareol and 3-oxosclareol.

9. A method according to claim 7, wherein 3β-hydroxysclareol is extracted from the said product for incorporation with the smoking material.

10. A smoke-flavour enhancing agent produced by the method according to claim 7.

* * * * *